(12) United States Patent
Hershey et al.

(10) Patent No.: US 8,777,900 B2
(45) Date of Patent: Jul. 15, 2014

(54) AMBULATORY ENTERAL FEEDING SYSTEM

(75) Inventors: Adrienne A. Hershey, Cumming, GA (US); Alison S. Bagwell, Alpharetta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 2 days.

(21) Appl. No.: 12/967,612

(22) Filed: Dec. 14, 2010

(65) Prior Publication Data

US 2012/0150112 A1 Jun. 14, 2012

(51) Int. Cl.
*A61M 37/00* (2006.01)

(52) U.S. Cl.
USPC ........................................ 604/131

(58) Field of Classification Search
USPC ........................ 604/131–134, 140
See application file for complete search history.

(56) References Cited

U.S. PATENT DOCUMENTS

| | | | |
|---|---|---|---|
| 4,270,533 A | 6/1981 | Andreas | |
| 4,356,824 A | 11/1982 | Vazquez | |
| 4,529,102 A | 7/1985 | Quinn et al. | |
| 4,576,603 A | 3/1986 | Moss | |
| 4,741,736 A * | 5/1988 | Brown | 604/134 |
| 4,850,971 A * | 7/1989 | Colvin | 604/134 |
| 5,330,431 A * | 7/1994 | Herskowitz | 604/153 |
| 5,336,188 A * | 8/1994 | Kriesel | 604/132 |
| 5,348,539 A * | 9/1994 | Herskowitz | 604/141 |
| 5,460,603 A | 10/1995 | DeSantis | |
| 5,468,226 A * | 11/1995 | Kriesel | 604/132 |
| 5,492,533 A * | 2/1996 | Kriesel | 604/132 |
| 5,681,284 A * | 10/1997 | Herskowitz | 604/141 |
| 5,693,019 A * | 12/1997 | Kriesel | 604/132 |
| 5,700,147 A * | 12/1997 | Mills et al. | 433/98 |
| 5,848,993 A * | 12/1998 | Tanhehco et al. | 604/217 |
| 6,447,472 B1 | 9/2002 | Moss | |
| 6,482,170 B1 | 11/2002 | Andersen | |
| 6,949,092 B1 | 9/2005 | Moss | |
| 7,018,361 B2 * | 3/2006 | Gillespie et al. | 604/151 |
| 7,048,727 B1 | 5/2006 | Moss | |

(Continued)

FOREIGN PATENT DOCUMENTS

| | | |
|---|---|---|
| EP | 0 096 849 A2 | 12/1983 |
| EP | 0 648 513 B1 | 3/1998 |
| JP | 2010-017180 A | 1/2010 |
| WO | WO 2007/095541 A2 | 8/2007 |

OTHER PUBLICATIONS

"Farrell Valve—Enteral Gastric Pressure Relief System," brochure, CORPAK MedSystems, Wheeling, IL, 2008, 2 pages.

(Continued)

*Primary Examiner* — Victoria P Shumate
(74) *Attorney, Agent, or Firm* — James B. Robinson

(57) ABSTRACT

There is provided a venting system for enteral feeding having a reflux bag in fluid communication with an enteral feeding site on a patient. The bag has a vent that relieves enteral pressure from the patient and is located within a bellows that compresses the reflux bag after the vent relieves. The system does not rely on gravity to urge the liquid in the reflux bag back to the patient so it may be used by sleeping patients who change positions. It may also be placed in a backpack so that the patient may be freed from having to remain seated or prone for long periods of time and can instead lead a more normal lifestyle.

8 Claims, 1 Drawing Sheet

(56) References Cited

U.S. PATENT DOCUMENTS

| | | |
|---|---|---|
| 2004/0054350 A1 | 3/2004 | Shaughnessy et al. |
| 2005/0124932 A1* | 6/2005 | Foster et al. ............... 604/99.04 |
| 2005/0124935 A1 | 6/2005 | McMichael |
| 2006/0224106 A1* | 10/2006 | Honchel ......................... 604/37 |
| 2008/0033345 A1 | 2/2008 | Langloss et al. |
| 2008/0033364 A1 | 2/2008 | Kamen et al. |
| 2008/0033365 A1 | 2/2008 | Solovay et al. |
| 2008/0039809 A1 | 2/2008 | Kamen et al. |
| 2008/0179882 A1* | 7/2008 | Hanlon et al. ................ 285/304 |
| 2009/0209917 A1* | 8/2009 | Tanaka et al. ................. 604/174 |
| 2010/0137746 A1* | 6/2010 | Holte ............................ 600/584 |

OTHER PUBLICATIONS

"Farrell Valve & Super Farrell Valve," directions for use, CORPAK MedSystems, Wheeling, IL, 2008, 1 page.

* cited by examiner

AMBULATORY ENTERAL FEEDING SYSTEM

The present disclosure relates to a system for venting in connection with enteral feeding, to reduce gas pressure and discomfort for patients.

Many patient feeding devices employ a gastrostomy feeding tube. One relatively common situation is to provide nutritional solutions or medicines directly into the stomach or intestines. A stoma is formed in the stomach or intestinal wall and a catheter is placed through the stoma. Such catheters generally have a base connector for tubing on the proximal end and a balloon on the distal to keep the catheter in place. Feeding solutions can be injected through the catheter at an enteral feeding site on the patient to provide nutrients directly to the stomach or intestines in a process known as enteral feeding. A variety of different catheters intended for enteral feeding have been developed over the years, including some having a "low profile" base connector relative to the portion of the catheter which sits on a patient's skin, as well as those having the more traditional or non-low profile configuration.

Enteral feeding may be necessary because of a number of causes, one of which is the not uncommon reaction following major surgery in which a patient's stomach function is impaired for a period of time. If the patient has a problem with gastric reflux or vomiting, for example, or if the stomach is not adequate for the patient's digestive process requirements, another feeding mode must be chosen. In addition to the need to supply or supplement the body with a certain level of nutrients and the like following surgery as well as in other instances of impaired or limited gastric functionality, a further issue is that an unfed gut can become a source of bacteria that gets into the bloodstream.

In enteral feeding, after the placement of the feeding head and catheter in the patient's body, nutrients are pumped from a bag into the catheter and into the stomach or intestine. The nutrient bag may be hung above the bed of the patient and the feeding pump placed nearby.

While the problems noted above can be solved by the introduction of nutrients through an enteral feeding device tube properly inserted through the patient's abdominal wall, a problem of pressure buildup in the intestines and/or stomach is quite common. This pressure buildup is the result of normal digestive processes but can be very painful, especially for pediatric patients. Typically the body relieves such excess gastric pressure through expulsion of accumulated gas or liquid through a burping response. However, in a patient undergoing enteral feeding in which fluid nutrients are being continually fed to the gastrointestinal tract, upward expulsion of gastric reflux materials is highly undesirable. More importantly, reflux of gas or liquid through the enteral feeding tube cannot occur.

Though gastric reflux pressure created by even limited episodes of stomach movement may exceed several feet of water, such reflux pressure is inadequate to overcome the greater forward fluid pressure present within the enteral feeding tube. This greater fluid pressure is developed because the height of the column of fluid nutrient in the enteral feeding system usually stands well above the level of the patient's stomach. Fluid pressure is further increased through the use of the enteral feeding pump. In addition, tube set clamps along the administration tubing also prevent reflux of excessive gastric gas or liquid through the enteral feeding tube.

Because gastric reflux pressure cannot overcome the greater forward fluid pressure within the enteral feeding tube, reflux materials may be expelled upward from the stomach through the esophagus and are expressed out of the mouth, where the enteral feeding tube is orally intubated, or through the nasal passages, where naso-pharyngeal intubation has been utilized. In the latter, it is possible for the patient to inhale the reflux materials into the lungs with possible risk of aspiration pneumonia. The problem of relief of gastric reflux pressure is most accute in neonates, infants and small children in which gastric pressure may rapidly accumulate through periodic episodes of crying and because such patients have yet to develop control over the burping response as a means of gastric pressure relief or have had a Nissen Fundoplication or other procedure that does not allow the burping response and gastric reflux to occur. However, it is not unusual for adult patients undergoing enteral feeding to experience occasional difficulties with gastric reflux pressure relief.

A number of possible solutions have been suggested to relieve pressure in the digestive tract. One widely used option is the Farrell valve available from Corpak® MedSystems of Wheeling Ill., described in U.S. Pat. No. 6,482,170. This system was developed to permit relief of gastric reflux pressure through the enteral feeding tube to avoid uncontrolled upward expulsion of reflux materials through the burping response. The Farrell valve uses a "Y" type connector that is placed in the feeding line between the feeding pump and the patient. An additional line is connected to the "Y" and terminates at a second or reflux bag hanging at the same height as the nutrient bag. The reflux bag is vented to the atmosphere in order to allow gas to escape the system. The "Y" connector is located below the level of the patient's stomach in order to keep at least a small amount of nutrient in the tubing line leading to the reflux bag. The small amount of nutrient prevents air from being introduced to the stomach from the reflux is bag, functioning in much the same manner as a plumbing system trap.

While the system of the '170 patent performs satisfactorily, the patient must be in a prone position or at least non-ambulatory in order to use it, since it requires that the nutrient bad and reflux bag be located at the same height of a few feet above the patient's stomach. Enteral feeding normally takes a significant amount of time, and this system can be difficult for older children and adults to use because their daily routines require them to move about to attend school or work.

There remains a need for a system that can relieve excess pressure from a patient's stomach and that is less obtrusive and unwieldy to use. An ambulatory system that may be placed, for example, in a backpack or shoulder pack and that will allow the user to go about his normal daily routine would be highly desirable.

SUMMARY

The present disclosure describes a venting system for enteral feeding having a reflux bag in fluid communication with an enteral feeding site on a patient. The reflux bag has a vent that relieves enteral pressure from the patient and is located within a bellows mechanism that compresses the bag after venting has occurred, expelling the built-up gas. Because the system does not rely on gravity but instead on mechanical compression of a reflux bag, the system can free the patient from the confines of a bed laying in the prone position, or chair and relieves gas pressure regardless of patient positioning or orientation.

The enteral venting system uses a mechanical compression or bellows system that may be an encircling or enclosing elastic member or members that expand and contract around a reflux bag. The bellows system may also be a rigid case to enclose the reflux bag with compression or torsion springs within the case to apply pressure to the reflux bag. In another embodiment, the bellows system may be an inflatable cuff that may be used to apply hydraulic or pneumatic pressure to the reflux bag, with the cuff pressure controlled by the patient or a caregiver. Another embodiment of the bellows system may be a semi-rigid or rigid case for the reflux bag with a foam material inside the case that acts as a spring. Another embodiment of the bellows system may be elastic materials that enclose the reflux bag at least partly and apply pressure to it.

The disclosed vent allows the entire nutrient delivery and venting system to be placed in, for example, a backpack or shoulder pack and worn by the patient, thus freeing the patient from a stationary and usually prone posture and allowing the patient to take part in other activities while receiving nutrients. This ambulatory system provides the patient more freedom and increases their quality of life.

The disclosed vent system also allows the entire system to be used while the patient is sleeping and moving around in their sleep, so the patient can sleep in different orientations yet still have automatic venting of enteral gases occur, i.e., venting without human interaction to cause the system to vent. This innovation increases the quality of the patient's and caregiver's sleep, allowing them to feel more rested and to function at a higher level while awake than would otherwise be the case because gas pressure is not waking them up to need to manually vent the patient.

Other objects, advantages and applications of the present disclosure will be made clear by the following detailed description of a preferred embodiment of the disclosure and the accompanying drawings wherein reference numerals refer to like or equivalent structures.

DETAILED DESCRIPTION

Reference will now be made to the drawings in which the various elements of the present disclosure will be given numeral designations and in which the disclosure will be discussed so as to enable one skilled in the art to make and use the disclosure. It is to be understood that the following description is only exemplary of the principles of the present disclosure, and should not be viewed as narrowing the pending claims. Those skilled in the art will appreciate that aspects of the various embodiments discussed may be interchanged and modified without departing from the scope and spirit of the disclosure.

Figure 1:
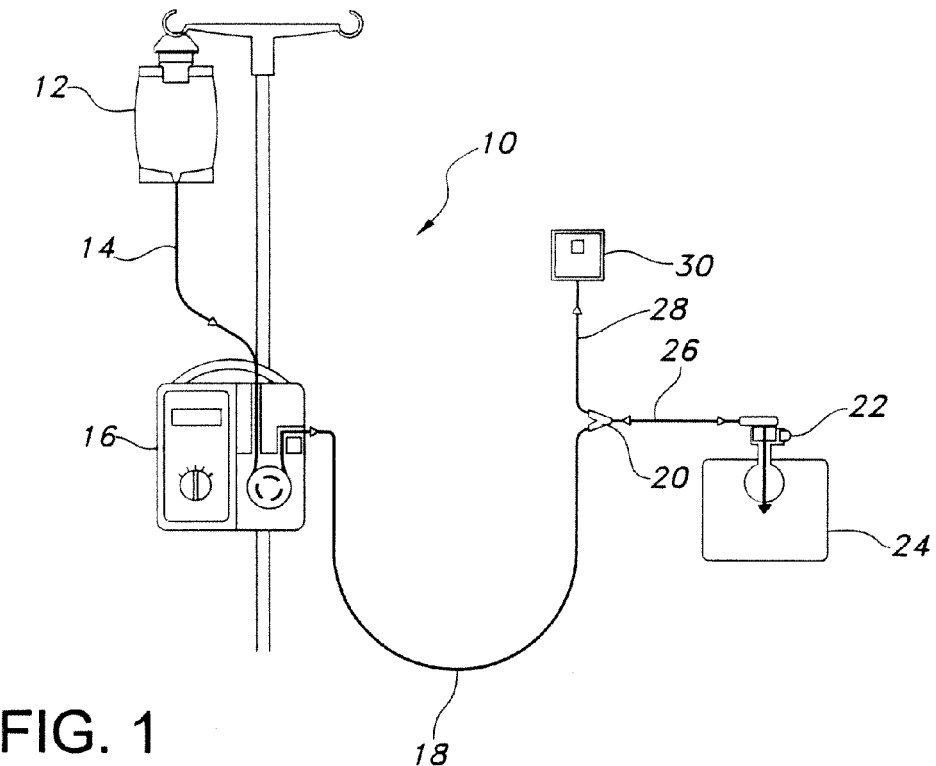
FIG. 1 is a perspective view of an enteral feeding system having a nutrient bag, a nutrient pump and ambulatory enteral feeding vent. The vent cassette is connected into the nutrient line between the pump and the enteral feeding site using a Y connector.

Turning to the drawings, FIG. 1 illustrates a general embodiment of the disclosed ambulatory enteral feeding system 10. The device 10 has a nutrient bag 12 containing a nutrient feeding formula for the patient 24. The nutrient formula is feed from the nutrient bag 12 to the nutrient pump 16 via tubing 14 and is discharged from the pump 16 to the enteral feeding site on the patient, again through tubing 18. A "Y" connector 20 is placed in the pump discharge line, i.e., between the pump 16 and the patient 24. An additional length of tubing 28 is connected between the "Y" connector 20 and a venting cassette 30. The patient 24 is equipped with a conventional enteral feeding base connector 22 (including a catheter and balloon as discussed above) for connection of the feeding tubing 26.

In regard to the proper nutrient feeding formulation, both formula characteristics and patient-specific factors need to be considered. Formula variables include: digestibility/availability of the nutrients, nutritional adequacy, viscosity, osmolality, ease of use, and cost. Patient variables include: nutritional status and requirements, electrolyte balance, digestive and absorptive capacity, disease state, renal function, medical or drug therapy, and possible routes available for administration. Adult enteral formula products fall into one of the following categories: general use, high nitrogen, high nitrogen and high calorie, fiber enriched, semi-elemental, fat modified, and specialty. Medical professionals such as dietitians are typically available to assist with formula selection, depending on the location. While the proper selection of nutrient formula for enteral feeding is very important for each individual patient, the myriad of products available makes an exhaustive discussion herein untenable. Suffice to note that the nutrient formulation may be the cause of many different patient complaints, including excessive abdominal pressure, and though the disclosed system can help alleviate pressure, the formulation should also be investigated as a possible cause.

The enteral feeding pump 16 is an electronic medical device that controls the timing and amount of nutrition delivered to a patient during enteral feeding. The enteral feeding pump ensures that the right amount of liquid is administered to the body over the course of a day. The amount of nutrition desired to be fed is entered into the electronic enteral feeding pump, which controls the flow of the nutrition so that the patient gets a measured amount of liquid continuously over a 24 hour period.

Patients who are administering enteral nutrition independently may choose to set their enteral feeding pump on a cyclic cycle. This can allow the patient to administer food over an eight-hour period throughout the night, permitting a more normal lifestyle without the pump during the day. Generally, an enteral feeding pump is very accurate, but problems in the electronic mechanisms can cause too much or too little nutrition to be administered to a patient. Many pumps come with safety features to make such an error extremely unlikely. An enteral feeding pump may have a "no single point of failure feature," so that the pump either has back-up mechanisms if one component fails, or an audible indication that the pump is clogged or no longer working. For devices used in stationary feeding settings, they may also come equipped with a battery pack to back up the unit if the normal electrical power has been dislodged.

Enteral feeding pumps are manufactured by a number of different suppliers. One example of a suitable pump system is available from Covidien A G of Mansfield, Mass. under the Kangaroo label. Pumps such as the Kangaroo Joey® and Kangaroo ePump® also have available backpacks and shoulder packs for ambulatory use, though no venting is provided. The backpack has two straps, one encircling each shoulder to support the pack. The shoulder pack has a single strap that encircles one shoulder and the pack rests on the hip of the wearer. Shoulder packs are regarded as somewhat less comfortable than backpacks since the pack tends to bump against the elbow of the wearer as he walks.

In the use of an enteral feeding system, the nutrient formula is pumped by the nutrient pump 16 from the nutrient bag 12, to the base connector 22 at the enteral feeding site on the patient 24. The proximal side of the base connector 22 is what remains outside the patient's body and it is through this connector that nutrients are provided to the patient. As noted, the base connector 22 has a proximal side and a distal side. It also includes a catheter with a lumen positioned through the base 22 and into the patient's stomach or intestine (as desired for the feeding location). A portion of the catheter extends away from the base on the distal or patient side. The distal end of the base connector of such a device/assembly usually includes a balloon which may be expanded to hold the connector 22 in position in the body after it is installed. A variety of different connectors intended for enteral feeding have been developed over the years, including some having a "low profile" relative to the portion of the catheter which sits on a patient's skin, as well as those having the more traditional or non-low profile configuration. U.S. Pat. No. 6,019,746 provides an example of such a device.

In the normal use of an enteral feeding system the nutrient formulation flows from the pump to the base connector and into the desired location in the patient's digestive tract; generally the stomach or intestines. Should there be a build-up of excess gas in the patient's stomach that cannot be relieved by the patient, for example due to a Nissen Fundoplication, the pressure in the patient's intestinal tract may match and perhaps exceed the pressure provided by the enteral feeding pump 16. If the pressure within the patient exceeds that of the pump discharge, fluid flow to the patient will stop and the nutrient formulation will back up in the nutrient tubing 26, eventually going through the "Y" connector 20 and vent tubing 28 to the cassette 30. The cassette will then have a mixture of liquid and gas within it. The nutrient formulation will generally not back up through the pump towards the nutrient bag since the pressure in the cassette is normally lower than the maximum pump discharge pressure. The build-up of pressure will continue until the entire system downstream of the pump reaches the maximum discharge pressure, also called the dead head pressure, of the pump or the venting pressure of the venting cassette 30, whichever is lower.

The venting system is comprised of a reflux bag 32 having at least one vent 36 thereon, and the vented reflux bag 32 is provided with a mechanical system to assist in returning the reflux bag 32 to its initial condition (or nearly so) after it has vented. The reflux bag 32 has a tubing connection 34 that allows connection to the vent tubing 28. The tubing connection 34 is desirably on the bottom of the reflux bag 32 so that any liquid that enters the reflux bag 32 can drain back to the tubing 28. The reflux bag 32 may be of any suitable shape; rectangular, square, circular, triangular, etc. The pliable reflux bag 32 (FIG. 4) may be made desirably from polymeric materials like polyolefins, polyesters, acrylics, mylar, and PTFE. The reflux bag 32 or the layers 38 may be provided with a hook or a hanging hole on its upper side to allow it be attached to a stand or other device if it is desired to use the disclosed device in a stationary setting.

In most embodiments, the mechanical bellows system is an encircling or enclosing elastic member or members that expand and contract. In the embodiments illustrated, the reflux bag 32 is sandwiched between two layers 38 of a relatively flexible polymer and the reflux bag 32 desirably has a nearly zero volume when it is empty. The layers 38 of polymer are adapted to elastically bend outwardly as the reflux bag 32 expands under pressure. This bending proceeds to the point at which the pressure is relieved by the vent 26 in the reflux bag 32. Once the pressure in the reflux bag 32 (and thus the entire system downstream of the nutrient pump) is relieved, the layers 38 return to approximately their starting positions, compressing the reflux bag 32. As the reflux bag 32 is compressed, liquid may be pushed back through the tubing connector 34 into the vent tubing 28 and on toward the patient 24. The layers 38 in this embodiment function as a bellows, expanding as the reflux bag 32 expands and contracting after the reflux bag 32 pressure is relieved.

Figure 2:
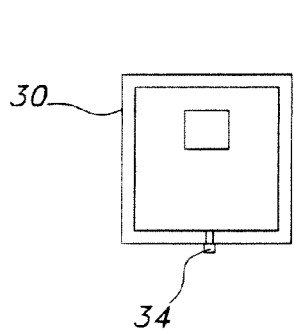
FIG. 2 is a front view of a ambulatory enteral feeding showing a tubing connection. While shown in a vertical position, the cassette may be placed in any convenient orientation provided the tubing connecting it to the rest of the system does not become kinked.
Figures 3, 4:
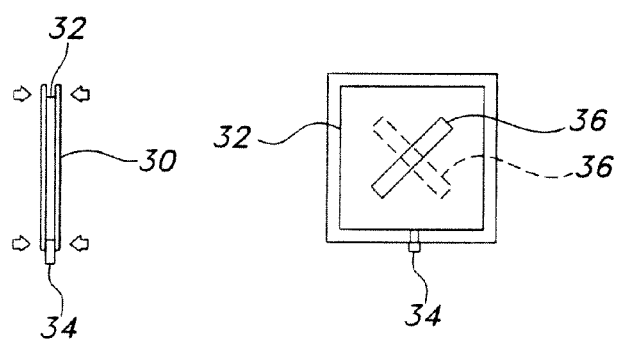
FIG. 3 is a side view of a ambulatory enteral feeding showing a venting bag between two layers of stiffer material. The stiffer material serves in this embodiment as the mechanical compression or bellows mechanism to help return the reflux bag to its initial shape and position after it has vented.
FIG. 4 is a perspective view of a venting bag having diagonal vents on the obverse and reverse sides. The vents may be arranged in virtually any functioning position though the orientation shown has been found to function well.

The cassette 30 is shown in FIGS. 2 and 3 and is a relatively small, durable and thin item for ease of transportation and general use. The layers 38 that comprise the sides of the venting cassette 30 as shown in the Figures may be made from many suitable materials and their thickness and other dimensions may be varied as needed. Desirable materials from which the layers of the cassette 30 may be made include polyolefins like polyethylene and polypropylene, polyamides, polyurethanes, PTFE and combinations thereof as well as elastomeric materials discussed at length below. Relatively flexible layers that will bend repeatedly without breaking are desirable so that the life of the cassette is not unmanageably short. The relative hardness of the polymers used to make the layers may be measured by the Shore hardness, a series of scales that is known to those skilled in the art. Hardness is measured using a device called a "durometer", an instrument specifically developed to measure relative hardness, and is usually performed following ASTM D2240. In the Shore A and D hardness or durometer scales, a higher number indicates a polymer that is harder than a polymer having a lower number within each scale. The Shore A and D scales are used for different types of polymers. Typically the Shore A scale is used for softer, more elastic polymers and the Shore D scale used for stiffer polymers. When comparing the Shore A and Shore D scales, low D values are typically harder than high A values. Desirably, the flexible layers of the disclosed device may have a Shore hardness between 50 A and 70 A. This is not meant to be a restrictive requirement, however, since the flexibility of the layers can also be manipulated by the variation of the thickness of the layers. A thick layer of a more elastic polymer, for example, may not perform as well as a thinner layer of a less elastic polymer. The choice of the materials of construction, as noted above, should be made by one skilled in the art considering the design requirements of the particular application. It should also be noted that the layers 38 need not be made from the same materials or be identical. For example, one of the layers could be stationary and the other layer movable, though for ease of construction identical layers 38 are probably desirable.

As noted above, other means of compressing the bag will also function suitably. Such other means include using a rigid case to enclose the reflux bag with compression or torsion springs within the case to apply pressure to the reflux bag. The springs may be metallic or plastic or of other suitable materials. In this case the reflux bag would be placed in the rigid case with a number of springs, desirably with a pressure distributing plate between the springs and the reflux bag. The plate would also serve to protect the reflux bag from possible piercing or other damage from the springs. The springs would be selected to provide the requisite pressure to assist in the contraction of the bag once the pressure was relieved.

Still other means of mechanically compressing the reflux bag include an inflatable cuff may be used to apply hydraulic or pneumatic pressure to the reflux bag, with the cuff pressure controlled by the patient or a caregiver. The inflatable cuff could be designed to encircle the reflux bag or could be present on only one side of the reflux bag. The reflux bag and cuff could be placed in a case to provide rigidity to the other side of the reflux bag. The cuff pressure could be any pressure desired by the patient or caregiver so that the patient's comfort could be assured.

Still other means include a semi-rigid or rigid case for the reflux bag having a foam material inside the case that acts as a spring. The foam could be approximately the same size as the reflux bag and could rest on one side of the reflux bag with the case on the other side of the reflux bag. As the reflux bag expanded the foam would be compressed against the inside of the case. Once the pressure was relieved from the reflux bag within the closed case, the foam would spring back towards its original shape, pushing any liquid in the reflux bag back towards the patient.

Elastic materials that enclose the reflux bag at least partly and apply pressure to it may also be used. A large band of elastic material that encircled the reflux bag, for example, would allow expansion of the reflux bag and then compress the reflux bag once it was relieved. Suitable elastic materials may be made from elastomeric polymers and may be in the form of non-woven fabrics produced by processes such as spunbonding and meltblowing. Laminates of elastomeric fibers produced by various methods may also be used. Such fabrics may be, for example, wound around the reflux bag in a predetermined number of turns to produce the needed elastic and mechanically compressive characteristics for the embodiment desired.

Elastomeric thermoplastic polymers useful for such a reflux bag enclosing embodiment may be those made from block copolymers such as polyurethanes, copolyether esters, polyamide polyether block copolymers, ethylene vinyl acetates (EVA), block copolymers having the general formula A-B-A' or A-B like copoly(styrene/ethylene-butylene), styrene-poly(ethylene-propylene)-styrene, styrene-poly(ethylene-butylene)-styrene, (polystyrene/poly(ethylene-butylene)/polystyrene, poly(styrene/ethylene-butylene/styrene) and the like.

Useful elastomeric resins include block copolymers having the general formula A-B-A' or A-B, where A and A' are each a thermoplastic polymer endblock which contains a styrenic moiety such as a poly (vinyl arene) and where B is an elastomeric polymer midblock such as a conjugated diene or a lower alkene polymer. Block copolymers of the A-B-A' type can have different or the same thermoplastic block polymers for the A and A' blocks, and the present block copolymers are intended to embrace linear, branched and radial block copolymers. In this regard, the radial block copolymers may be designated $(A-B)_m-X$, wherein X is a polyfunctional atom or molecule and in which each $(A-B)_m$-radiates from X in a way that A is an endblock. In the radial block copolymer, X may be an organic or inorganic polyfunctional atom or molecule and m is an integer having the same value as the functional group originally present in X. It is usually at least 3, and is frequently 4 or 5, but not limited thereto. Thus, in the present invention, the expression "block copolymer", and particularly "A-B-A" and "A-B" block copolymer, is intended to embrace all block copolymers having such rubbery blocks and thermoplastic blocks as discussed above, which can be extruded (e.g., by meltblowing), and without limitation as to the number of blocks. The elastomeric nonwoven web may be formed from, for example, elastomeric (polystyrene/poly (ethylene-butylene)/polystyrene) block copolymers. Commercial examples of such elastomeric copolymers are, for example, those known as KRATON® materials which are available from Kraton Polymers of Houston, Tex. KRATON® block copolymers are available in several different formulations, a number of which are identified in U.S. Pat. Nos. 4,663,220, 4,323,534, 4,834,738, 5,093,422 and 5,304,599, hereby incorporated by reference.

Polymers composed of an elastomeric A-B-A-B tetrablock copolymer may also be used in the practice of the disclosed device. Such polymers are discussed in U.S. Pat. No. 5,332,613 to Taylor et al. In such polymers, A is a thermoplastic polymer block and B is an isoprene monomer unit hydrogenated to a substantially a poly(ethylene-propylene) monomer unit. An example of such a tetrablock copolymer is a styrene-poly(ethylene-propylene)-styrene-poly(ethylene-propylene) or SEPSEP elastomeric block copolymer available from Kraton Polymers.

Other exemplary elastomeric materials which may be used include polyurethane elastomeric materials such as, for example, those available under the trademark ESTANE® from Lubrizol of Wickliffe, Ohio or MORTHANE® from Morton International Inc., polyester elastomeric materials such as, for example, those available under the trade designation HYTREL® from E. I. DuPont De Nemours & Company, and those known as ARNITEL®, available from DSM of Sittard, Holland.

As used herein the term "spunbonded fibers" refers to small diameter fibers which are formed by extruding molten thermoplastic material as filaments from a plurality of fine, usually circular capillaries of a spinneret with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, and U.S. Pat. No. 3,542,615 to Dobo et al. Spunbond fibers are generally not tacky when they are deposited onto a collecting surface. Spunbond fibers are generally continuous and have average diameters (from a sample of at least 10) larger than 7 microns, more particularly, between about 10 and 20 microns. The fibers may also have shapes such as those described in U.S. Pat. No. 5,277,976 to Hogle et al., U.S. Pat. No. 5,466,410 to Hills and U.S. Pat. Nos. 5,069,970 and 5,057,368 to Largman et al., which describe fibers with unconventional shapes.

As used herein the term "meltblown fibers" means fibers formed by extruding a molten thermoplastic material through a plurality of fine, usually circular, die capillaries as molten threads or filaments into converging high velocity, usually hot, gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al. Meltblown fibers are microfibers which may be continuous or discontinuous, are generally smaller than 10 microns in average diameter, and are generally tacky when deposited onto a collecting surface.

As used herein "multilayer nonwoven laminate" means a laminate wherein some of the layers are spunbond and some meltblown such as a spunbond/meltblown/spunbond (SMS) laminate and others as disclosed in U.S. Pat. No. 4,041,203 to Brock et al., U.S. Pat. No. 5,169,706 to Collier, et al, U.S. Pat.

No. 5,145,727 to Potts et al., U.S. Pat. No. 5,178,931 to Perkins et al. and U.S. Pat. No. 5,188,885 to Timmons et al. Such a laminate may be made by sequentially depositing onto a moving forming belt first a spunbond fabric layer, then a meltblown fabric layer and last another spunbond layer and then bonding the laminate in a manner described below. Alternatively, the fabric layers may be made individually, collected in rolls, and combined in a separate bonding step. Such fabrics usually have a basis weight of from about 0.1 to 12 osy (6 to 400 gsm), or more particularly from about 0.75 to about 3 osy. Multilayer laminates may also have various numbers of meltblown layers or multiple spunbond layers in many different configurations and may include other materials like films (F) or coform materials, e.g. SMMS, SM, SFS, etc.

s As mentioned previously, gas pressure builds in the cassette 30 because of a build-up of pressure within the patient's digestive system that cannot be relieved in any other manner. Once the gas pressure reaches the pressure selected for the vent, the pressure will be relieved by the cassette 30 and liquid nutrients returned to the patient via the vent tubing 28, "Y" connector 20 and base tubing 26. The vent 36 is adapted to relieve pressure from the reflux bag 32 at a pressure of about 0.5 pounds per square inch (psi) (3.48 kilopascal) (kPa), the pressure at which it has been documented that pain from stomach gas pressure starts to be felt. Other vent pressure relief points may be chosen depending on medical factors related to a specific patient, so the relief pressure may be from 0.2 to 0.8 psi (1.4 to 5.5 kPa). The vent pressure may be chosen by varying the type or number of layers of the materials from which the vent is made. A highly porous vent material, for example, will vent before a less porous material will vent. Similarly, a single layer vent material will vent before a multi-layer vent made from the same material will vent.

The vent 26 may be of any convenient shape and there is desirably at least one vent 26 on either side of the reflux bag 32. One suitable arrangement for the vent(s) 36 is shown in FIG. 4 wherein one vent 36 is shown as a diagonal line on the reflux bag 32 on the obverse side. A second vent 36 could be placed on the reverse side of the reflux bag 32, for example on a diagonal that is not parallel to the vent 36 on the obverse side. FIG. 4 shows one embodiment using two vents is shown where the reverse side vent 36 is shown as a dashed line. It is important, of course, that any of the mechanical systems used to enclose the reflux bag do not cover the vent in such a manner as to prevent it from venting. The use of an elastomeric non-woven material to encircle the reflux bag, for example, should be done with care, taking into account the breathability characteristics of the non-woven fabric, should it be placed over the vent.

The vent 36 desirably comprises a membrane that may be a nonwoven material that is placed over a slit or hole in the reflux bag 32. The membrane material may be glued to the edges of the slit in the bag using any suitable adhesive or may be heat sealed (welded) or attached in other ways known to those skilled in the art. Heat sealing, for example, uses heat, pressure and dwell time to thermally bond thermoplastic materials together. Heat sealing devices generally have a press with a set of jaws that open (vertically), into which the materials to be bonded are placed. The jaws are heated by, for example, electric resistance heating and the temperature of each may be controlled separately. The pressure at which the jaws come together may also be adjusted for optimal bonding. Lastly, the time for which the jaws are together (the "dwell" or "hover" time) may also be adjusted. A dwell time of zero indicates that the jaws were brought together for an instant and immediately moved apart, i.e., they were not held together.

The size of the vent 36 may vary slightly depending on the porosity of the membrane material used. In the embodiment shown in FIG. 4, each vent is about 5 square centimeters in size for a total of about 10 square cm for the reflux bag. Vent sizes as low as 1 square cm and as great as 30 square cm can be used through extremely large vent areas may comprise the structural integrity of the reflux bag somewhat and make the reflux bag difficult to handle.

The vent membrane materials are generally hydrophobic in order to retain liquid within the reflux bag while allowing gas to pass through it. These materials are also hydrophobic because it is important that the membrane material not become degraded by contact with any liquid present in the bag.

Suitable nonwoven membrane materials include microporous materials such as Millipore® DVSP vent membrane using Surevent® PVDF membrane material with a 0.65 micron pore size, Millipore® BVSP vent membrane using Surevent® PVDF membrane material with a 1 micron pore size, Millipore® BVSPW vent membrane using Surevent® PVDF membrane material with a 1 micron pore size, Millipore® DOHP vent membrane using Surevent® UPE membrane material with a 0.65 micron pore size, Millipore® UPBP vent membrane using Surevent® UPE membrane material with a 1 micron pore size, Millipore® BPTFEPP vent membrane using Surevent® PTFE membrane material with a 1 micron pore size, Millipore® BPTFEPE vent membrane using Surevent® PTFE membrane material with a 1 micron pore size, Gore® MMT 332 vent membrane with expanded PTFE membrane material with a 1 micron pore size, Porex® vent membrane with Mupor® PTFE membrane material with a 4 micron pore size, Porex® vent membrane with X-7744PE membrane material with a 10 micron pore size, Pall® vent membrane with Versapor® 800R (acrylic) membrane material with a 0.8 micron pore size and Pall® vent membrane with Versapor® 500R (acrylic) membrane material with a 5 micron pore size.

Millipore® materials are available from Millipore® Corporation of Billerica, Mass. Gore® materials are available from WL Gore® & Associates of Newark, Del. Porex® materials are available from Porex® Corporation of Fairburn, Ga. Pall® materials are available from Pall® Corporation of Port Washington, N.Y.

Since the venting mechanism disclosed herein does not rely on gravity to force nutrients back to the patient, as does the system of U.S. Pat. No. 6,482,170 for example, the cassette need not be placed high above the patient. This allows the entire nutrient delivery and venting system to be placed in a condensed volume, for example, a backpack that may be worn by the patient. This frees the patient from a stationary and usually prone posture and allows the patient to take part in other activities while receiving nutrients. This ambulatory system provides the patient more freedom and a better quality of life.

In one embodiment, the reflux bag 32 may be flat and rectangular and approximately 8.5 cm wide on the side having the tubing connection 34 and the side opposite, and about 10 cm wide on the sides that are perpendicular to the tubing connection 34. The layers 38 may be square and about 10 cm by 10 cm, connected to each other on the sides perpendicular to the tubing connection 24 but open on the other two sides to allow insertion of the reflux bag 32 between the layers 38 and to allow movement of the layers 38 relative to each other. The layers 38 may be about 3 mm thick and made from a polymeric plastic material having sufficient flexibility. The reflux bag may be polyethylene and the vent membrane attached to the reflux bag by heat sealing, giving a total vent area of about 10 square cm. The venting cassette will accept liquid and gas from the patient as the pressure in the patient's digestive system increases. As this occurs the layers will slowly flex or bend outwardly, allowing the reflux bag to expand. At a pressure of about 0.5 psi, the vent membrane will allow the gas present in the reflux bag to pass through itself to the outside atmosphere and the layers will slowly move back towards their original positions. As this occurs the liquid that was present in the reflux bag will exit the reflux bag via the tubing connection 24 and flow back towards the patient, ultimately passing through the base connector to the digestive system of the patient.

In another embodiment, the reflux bag may be wrapped with an elastomeric nonwoven fabric comprised of, for example, Kraton® elastic fibers made by the meltblowing process. As the reflux bag accepts liquid and gas from the patient, the reflux bag slowly fills and expands and the pressure in the system increases until it reaches the pressure of about 0.5 psi. The membrane then allows the gas to vent, maintaining the liquid inside the reflux bag, and the elastomeric fibers surrounding the reflux bag urge the reflux bag back to nearly its starting configuration. The liquid in the reflux bag travels back through the tubing to the patient.

It should be noted that while the disclosed venting system is described above as being connected to the "Y" connector 20 via vent tubing 28, it is also possible to connect the system directly to the enteral feeding base connector 22 without the administration of nutrients. In such a case, the cassette 30, for example, may be connected to the base connector 22 without the balance of the feeding system, i.e. the pump 16 and nutrient bag 12 and all the associated tubing. The use of the system in this manner would allow the relief of pressure that has built-up within a patient's digestive system between feedings, for example, for reasons that may be unconnected to enteral feeding or to the enteral feeding solution being used.

In yet another embodiment, the cassette 30 may be connected to the base connector 22 while simultaneously connecting the balance of the feeding system to the base connector 22 by using a "T" fitting at the base connector 22 instead of a connector in the tubing line. This may be more convenient for the patient or medical personnel in some situations.

As used herein and in the claims, the term "comprising" is inclusive or open-ended and does not exclude additional unrecited elements, compositional components, or method steps.

While the disclosure has been described in detail with respect to specific embodiments thereof, it will be apparent to those skilled in the art that various alterations, modifications and other changes may be made to the disclosure without departing from the spirit and scope of the present disclosure. It is therefore intended that the claims cover all such modifications, alterations and other changes encompassed by the appended claims.

We claim:

1. A venting system for enteral feeding comprising an enteral feeding gastrostomy site that allows nutritional solutions or medicines directly into a stomach or intestines of a patient through a stoma through a wall of said stomach or intestines, a bag in fluid communication with said site, said bag receiving enteral digestive gas from said patient, said bag having a vent and being located within a bellows that compresses said bag after said vent allows said enteral digestive gas from said patient to escape the venting system.

2. The venting system of claim 1 wherein said vent relieves at a pressure of between 1.4 and 5.5 kPa.

3. The venting system of claim 1 wherein said vent relieves at a pressure of about 3.48 kPa.

4. The venting system of claim 1 wherein said vent comprises a slit or hole in said bag and said slit or hole is covered with a nonwoven fabric that is a microporous membrane material.

5. A venting system for enteral feeding comprising a bag in fluid communication with an enteral feeding gastrostomy site on a patient, said bag having a vent, said bag located within a means for compressing said bag after said vent allows said digestive gas to escape the venting system, without human interaction.

6. The venting system of claim 5 wherein said vent relieves at a pressure of between 1.4 and 5.5 kPa.

7. The venting system of claim 5 wherein said vent relieves at a pressure of about 3.48 kPa.

8. The venting system of claim 5 that system relieves gas pressure regardless of patient positioning or orientation.

\* \* \* \* \*